United States Patent [19]
Dahlberg et al.

[11] Patent Number: 5,814,091
[45] Date of Patent: Sep. 29, 1998

[54] ACTIVE MEDICAL IMPLANT HAVING A HERMETICALLY SEALED CAPSULE AND METHOD FOR MAKING SAME

[75] Inventors: Kenneth Dahlberg, Stockholm; Ulf Lindegren, Enskede, both of Sweden

[73] Assignee: Pacesetter AB, Solna, Sweden

[21] Appl. No.: 822,729

[22] Filed: Mar. 24, 1997

[30] Foreign Application Priority Data

Mar. 26, 1996 [SE] Sweden ................................. 9601155

[51] Int. Cl.⁶ .................................................. A61N 1/375
[52] U.S. Cl. .................................................. 607/36
[58] Field of Search .................................................. 607/36

[56] References Cited

U.S. PATENT DOCUMENTS

| | | |
|---|---|---|
| 3,926,198 | 12/1975 | Kolenik . |
| 4,127,134 | 11/1978 | Ushakoff . |
| 4,248,237 | 2/1981 | Kenny . |
| 4,254,775 | 3/1981 | Langer ....................... 607/37 |
| 5,131,388 | 7/1992 | Pless et al. . |
| 5,144,946 | 9/1992 | Weinburg et al. . |

FOREIGN PATENT DOCUMENTS

| | | |
|---|---|---|
| 2466256 | 4/1981 | France . |
| 2 055 296 | 3/1981 | United Kingdom . |

*Primary Examiner*—William E. Kamm
*Assistant Examiner*—Carl H. Layno
*Attorney, Agent, or Firm*—Hill & Simpson

[57] ABSTRACT

An active medical implant has a hermetically sealable capsule formed by a first part and a second closing part, the capsule being devised to hold a battery unit, an electronics unit, conductors for electrically connecting the battery to the electronics unit, and contacts arranged on the exterior of the capsule for connection to electrodes. The first part is made, at least in part, of a rolled, multi-layer composite sheet or plate, one layer of which is made of a biocompatible material and a second layer of which is made of a diffusion-proof material which is essentially resistant to corrosive chemicals. The two layers are joined by rolling, with the layer made of biocompatible material constituting the outer wall of the capsule. The closing part contains a layer of the biocompatible material serving as the capsule's outer wall and a partition wall made of diffusion-proof material which is essentially resistant to corrosive chemicals, is arranged to form a first essentially closed space for the power source in the first part. A second space for the electronics unit is formed between the wall closing the capsule and the partition wall.

24 Claims, 2 Drawing Sheets

ACTIVE MEDICAL IMPLANT HAVING A HERMETICALLY SEALED CAPSULE AND METHOD FOR MAKING SAME

BACKGROUND OF THE INVENTION

1. Field of the Invention

The present invention is directed to an active medical implant, such as having a pacemaker or a defibrillator, having an encapsulated battery unit/power source, as well as a method for the manufacture of such an implant.

As used herein "battery unit" means essentially all parts of the battery excluding the casing.

2. Description of the Prior Art

Devices are intended for use as implants for administering medical therapy in the form of electrical pulses. The devices can encompass pulse-generating and, possibly, sensing circuits in addition to batteries. These types of devices are well-known in the medical art and are used with good results.

There has always been some concern about the effect that moisture, which surrounds the implanted device, could have on the device's casing, since the device inside the casing must be able to operate continuously for a number of years, impervious to surrounding human tissue, for reliable functioning. Conventionally, this is achieved by encapsulating the device in a hermetically sealed casing, as set forth in e.g. U.S. Pat. No. 4,127,134, to prevent damage caused by e.g. increased internal pressure resulting from the emission of gas by the battery during operation.

The aforementioned devices must also be protected from damage inflicted by their electrical components. These components are essentially inert, but batteries, capacitors etc. constitute potential risks if they are not carefully encapsulated.

U.S. Pat. No. 5,144,946 describes e.g. a pacemaker in which a battery and an integral connective unit are arranged in a casing having two parts. This unit contains the electrical components, conductors for interconnecting the battery and electrical circuits and terminals for transmitting signals from the pacemaker to the patient. In one embodiment, the integral connective unit is enclosed in a capsule made of e.g. silicone rubber, i.e. the electrical components are insulated from the battery to protect the electrical components.

One example of encapsulation of non-inert components, a capacitor in this instance, in devices of the above type is described in U.S. Pat. No. 5,131,388. This document also describes the importance of adapting the size of devices intended for use as implants. The document stipulates the use of a material with good corrosion resistance, such as stainless steel or titanium, for encapsulating the capacitor. Encapsulation of a conventional aluminum electrolytic capacitor, however, is involved in this instance.

Another problem to be considered with devices of this kind is the need to arrange a large number of components during assembly in a manner which saves space and is satisfactory from the safety point of view.

Conventionally, it has proved necessary with devices of the above kind, which utilize lithium-iodine batteries, to encapsulate the battery because battery iodine could attack the electronics or external casing. Titanium is not suitable for this casing, however, because titanium and even the titanium oxide which forms on it are attacked by iodine. So some other material must be found for battery encapsulation.

In order to protect the device from body fluids and achieve a device which is largely biocompatible, titanium is used to advantage for the external casing, since it has proved to be the most biocompatible material.

SUMMARY OF THE INVENTION

An object of the present invention is to provide a device of the aforementioned kind which is reliable, i.e. which protects components and which is suitable for the environment in which it is to be placed.

An additional object is to achieve such a device which is easy to assemble and seal.

An additional object is to achieve such a device of the aforementioned kind with small dimensions.

The above object is achieved in accordance with the principles of the present invention in an active medical implant, and a method for making same, wherein a hermetically sealed capsule is formed by a first part having a receptacle therein and a second part which closes the first part, the receptacle of the first part holding a battery unit and an electronics unit, with the first part being made, at least in part, of a multi-layer material having a first layer of a biocompatible material and a second layer which is substantially diffusion-proof and is substantially corrosion-resistant. The two layers are joined by rolling. The layer of biocompatible material constitutes the exterior wall of the capsule. The second part, which closes the opening in the upper portion of the first part, is formed at least by a layer of the biocompatible material. A partition wall, made of a material which is substantially corrosion-resistant and which is also substantially diffusion-proof, is disposed in the first part so as to form a closed space for the battery unit, with the lower portion of the first part and the partition wall constituting a casing for the battery unit, this casing being an integral part of the capsule. The presence of the partition wall also thereby forms a second space in the first part, in which the electronics unit is disposed.

DESCRIPTION OF THE PREFERRED EMBODIMENTS

Figure 1:
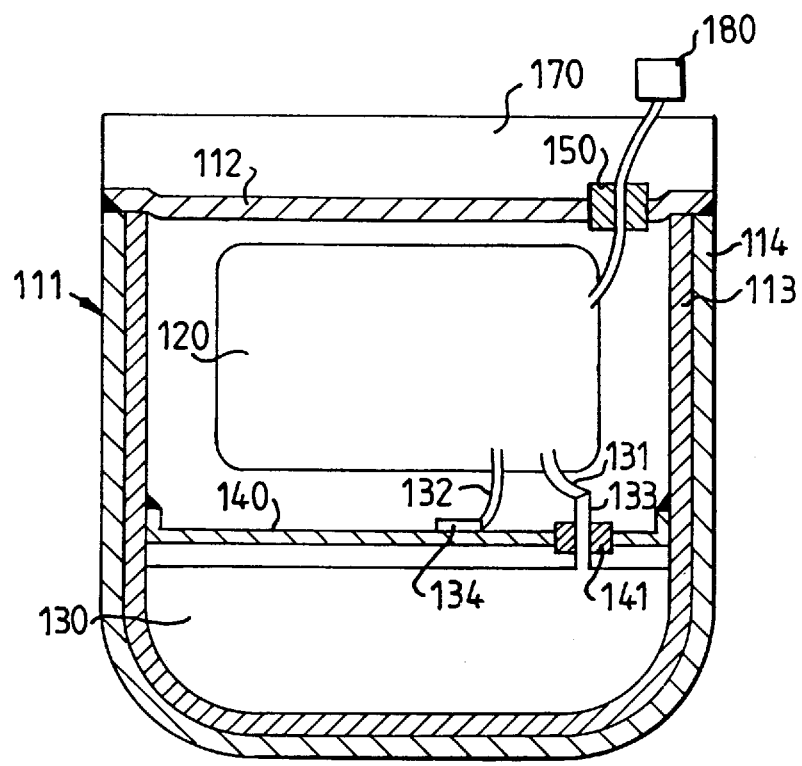
FIG. 1 shows a schematic cross-section of a first unipolar embodiment of the invention.

The active implant shown in FIG. 1 has a capsule made of two parts. A first part 111 is bowl-shaped and a second part 112 is arranged to seal the capsule. The capsule contains an electronics unit 120 of the kind used in these devices (not described herein), a battery unit 130 and conductors 131 and 132 between the battery unit and the electronics unit 120. An end section 170 is arranged on the closing part 112.

According to the invention, the first capsule part 111 is made of a rolled composite plate or sheet formed by two layers, i.e. one layer 113 made of stainless steel, and one layer 114 made of biocompatible material such as titanium. If stainless steel is used as the material for the layer 113, preferably 304L stainless steel is used (according to ASTM). The layer 113 could be replaced by some other suitable material, capable of functioning in concert with titanium, which is sufficiently dense and corrosion-resistant such as nickel or Cr-Ni steel. The layer 114 of titanium serves as the contact with the patient, and the stainless steel layer 113 is arranged on the interior of the part 111. The closing part 112 can, as here, be devised in the shape of a flat, titanium lid which is welded to the bowl-shaped part. The lid could also be made from the same combination of metals as the bowl-shaped part. A battery unit 130 is arranged in a first part of the device. The battery unit is separated from the rest of the capsule by a partition wall 140 made of stainless steel, e.g. 0.3 to 0.4 mm in cross-section, arranged essentially parallel to the bottom of the capsule and sealingly welded to the interior of the bowl-shaped part. A feedthrough 141 is arranged in the partition wall 140 for the battery's negative pole 133. In this example, the capsule serves as the positive pole, and a positive terminal 134 is arranged on the partition. The partition 140 can also be made of a number of layers, as long as the layer closest to the battery is a material of the same kind stipulated above.

The layer 113 thus serves as the battery's casing and is in direct contact with one of the electrodes and the electrolyte respectively.

An electronics unit 120, for which the battery serves as a source of current/power, is arranged in the second part of the capsule.

A feedthrough 150 is arranged through the closing part 112 for conductors from the electronics unit 120 to contacts intended for connection to heart electrodes.

Figure 2:
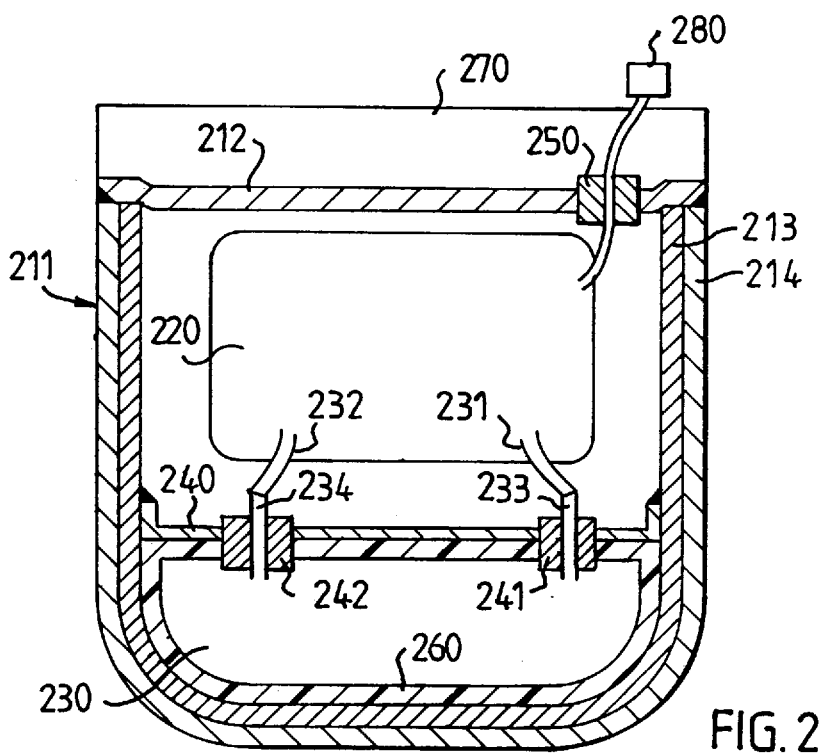
FIG. 2 shows a schematic cross-section of a second bipolar embodiment of the invention.

The active implant shown in FIG. 2 also has a capsule made of two parts. A first part 211 is bowl-shaped, and a second part 212 closes the capsule. The capsule contains an electronics unit 220 of the kind used in such devices (not described here), a battery unit 230 and conductors 231 and 232 respectively between the battery unit and the electronics unit. An end piece 270 is arranged on the closing part 212.

According to the invention, the first capsule part 211 is made of a rolled composite plate or sheet formed by two layers of metal, i.e. a layer 213 made of stainless steel and a layer 214 made of titanium. The layer 214 of titanium serves as the contact with the patient, and the stainless steel layer 213 is arranged on the interior of the part 211. The closing part 212 can, as here, be devised in the shape of a flat titanium lid which is welded to the bowl-shaped part. The lid could also be made from the same combination of metals as the bowl-shaped part. A battery unit 230 is arranged in a first part of the device. This unit is separated from the rest of the capsule by a partition wall 240 made of stainless steel, 0.3 to 0.4 mm in cross-section, arranged essentially parallel to the bottom of the capsule, and feedthrough 241 and 243 are arranged in the partition wall 240 for the battery's poles. In this embodiment, the battery unit is electrically insulated from surrounding metal surfaces by a non-conductive layer 260.

An electronics unit 220, for which the battery serves as a source of power, is arranged in the second part of the capsule.

A feedthrough 250 is arranged through the closing part 212 for conductors from the electronics unit to contacts intended for connection to electrodes.

In this embodiment, the capsule casing is not employed as one of the battery poles, and the battery is completely encapsulated in an insulating material which serves as the battery's casing encapsulating electrodes and electrolyte.

The invention also includes two types of encapsulated battery units, devised essentially like the battery section in the two aforementioned embodiments. The embodiments of these batteries are shown in FIGS. 3 and 4.

Figure 3:
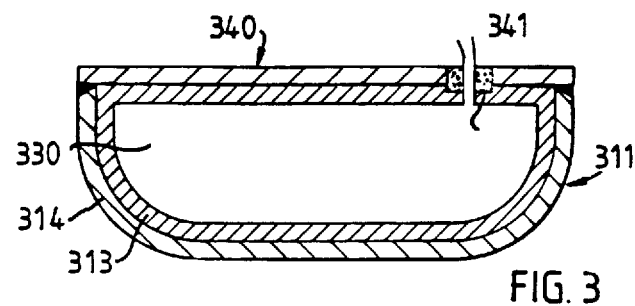
FIG. 3 shows a battery using the principle of the embodiment in FIG. 1.
Figure 4:
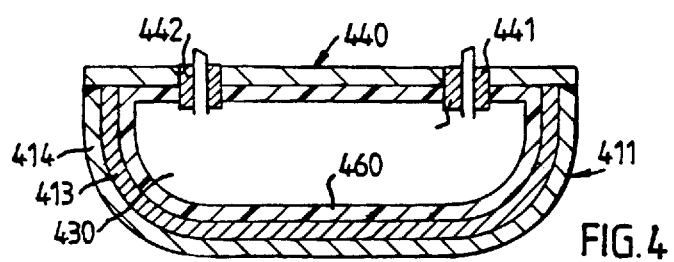
FIG. 4 shows a battery using the principle of the embodiment in FIG. 2.

The battery shown in FIG. 3 has a capsule with two parts. A first part 311 is bowl-shaped, and a second part 340 is arranged to close the capsule. A power source 330, e.g. a battery unit, is arranged in the capsule.

The first and second capsule parts 311 and 340 are made of two layers 313 and 314 of a rolled composite plate or sheet in the same way described for the part 111 in the description of FIG. 1.

The second closing part 340 is preferably made of the same combination of materials as the part 311 and is sealed to the first part 311. A feedthrough 341 is arranged in the second part for one of the battery poles. In this embodiment, the casing, or a part of the casing, serves as the other pole. Thus the layer 313 acts as the battery's casing and is in direct contact with electrode or electrolyte.

The power source shown in FIG. 4 has a capsule with two parts. A first part 411 is bowl-shaped, and a second part 440 is arranged to seal the capsule, e.g. by welding.

The first capsule part 411, is made of the same rolled-composite plate or sheet formed by two layers of metal 413 and 414 in the same way described in connection with FIG. 1. The second capsule part 440 is e.g. made from the same metal as the outer layer of the first part 411. The second part 440 may, of course, be made from the same metal plate/sheet combination as the first part 411.

The battery unit in the embodiment shown in FIG. 4 is electrically insulated from the casing/capsule by a non-conductive layer 460.

In the second part 440, feedthroughs 441 and 443 are arranged for the battery's poles.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an active medical implant having a battery and an electronics unit, the improvement comprising:

a hermetically sealed capsule comprising a first part having a receptacle therein and comprising, at least in part, a multi-layer material having a first layer consisting of a biocompatible material and a second layer consisting of a substantially diffusion-proof and substantially corrosion-resistant metal, said first layer and said second layer being joined together with said layer of biocompatible material comprising an exterior wall of said first part;

a second part, closing an upper opening in said first part, and comprised of at least said biocompatible material;

a partition wall disposed in said receptacle in said first part and having a surface facing away from said upper opening, said partition wall comprising a substantially diffusion-proof, corrosion-resistant metal at least at said surface and forming a first closed space in said first part in which said battery is disposed with said partition wall and a portion of said first part constituting a casing for said battery completely surrounding said battery with substantially diffusion-proof, corrosion-resistant metal, said casing being an integral part of said first part; and said partition wall and said second part forming a second closed space in said first part in which said electronics unit is disposed.

2. An active medical implant as claimed in claim 1 wherein said substantially diffusion-proof, corrosion-resistant metal of said second layer comprises a metal selected from the group consisting of stainless steel, nickel and Cr-Ni steel.

3. An active medical implant as claimed in claim 1 wherein said substantially diffusion-proof, corrosion-resistant metal of said second layer comprises 304L stainless steel.

4. An active medical implant as claimed in claim 1 wherein said biocompatible material comprises titanium.

5. An active medical implant as claimed in claim 1 wherein said battery has first and second poles, wherein said battery is in direct contact with said second layer of said first part, said second layer comprising a first of the poles of said battery and being connected to said electronics unit, and said active medical implant further comprising a feedthrough extending through said partition wall for connecting a second of the poles of the battery to said electronics unit.

6. An active medical implant as claimed in claim 1 wherein said battery has first and second poles, and said active medical implant further comprising first and second feedthroughs in said partition wall for respectively connecting said poles of said battery to said electronics unit.

7. An active medical implant as claimed in claim 1 wherein said substantially diffusion-proof, corrosion-resistant metal of said partition wall comprises a metal selected from the group consisting of stainless steel, nickel and Cr-Ni steel.

8. An active medical implant as claimed in claim 1 wherein said substantially diffusion-proof, corrosion-resistant metal of said partition wall comprises 304L stainless steel.

9. A battery unit for a medical implant comprising:
  a first part comprising at least in part a multi-layer material having a first layer consisting of a biocompatible material and a second layer consisting of a substantially diffusion-proof and corrosion-resistant metal, said first and second layers being joined together with said first layer forming an exterior wall of said first part, said first part forming a receptacle;
  a battery disposed in said receptacle; and
  a cover hermetically closing said receptacle and comprising at least one layer of a substantially diffusion-proof and corrosion-resistant metal and forming a closed space, with said first part, in which said battery unit is disposed and constituting a battery casing completely surrounding said battery with substantially diffusion-proof, corrosion-resistant metal.

10. A battery as claimed in claim 9 wherein said substantially diffusion-proof, corrosion-resistant metal of said second layer comprises a metal selected from the group consisting of stainless steel, nickel and Cr-Ni steel.

11. A battery as claimed in claim 9 wherein said substantially diffusion-proof, corrosion-resistant metal of said second layer comprises 304L stainless steel.

12. A battery as claimed in claim 9 wherein said biocompatible material comprises titanium.

13. A battery as claimed in claim 9 wherein said battery has first and second poles, wherein said second layer comprises one of said poles of said battery, and said battery further comprising an insulated feedthrough disposed in said cover connected to a second of said poles of said battery.

14. A battery as claimed in claim 9 wherein said battery has first and second poles, and said battery further comprising first and second insulated feedthroughs in said closing wall respectively connected to said poles of said battery.

15. An active medical implant as claimed in claim 9 wherein said substantially diffusion-proof, corrosion-resistant metal of said partition wall comprises a metal selected from the group consisting of stainless steel, nickel and Cr-Ni steel.

16. An active medical implant as claimed in claim 9 wherein said substantially diffusion-proof, corrosion-resistant metal of said partition wall comprises 304L stainless steel.

17. A method for manufacturing a casing for an active medical implant comprising:
  selecting a first sheet layer of a biocompatible material;
  selecting a second sheet layer of a substantially diffusion-proof, corrosion-resistant material;
  rolling said first and second sheet layers together to form a composite, multi-layer sheet;
  forming said composite, multi-layer sheet into a bowl-shaped receptacle;
  placing a battery in said receptacle, said battery having first and second poles; and
  hermetically sealing said receptacle with a second part and disposing at least one insulated feedthrough in said second part connected to one of said poles of said battery.

18. In an active medical implant having a battery and an electronics unit, the improvement comprising:
  of a hermetically sealed capsule comprising a first part having a receptacle therein and comprising, at least in part, a multi-layer material having a first layer consisting of a biocompatible material and a second layer consisting of a substantially diffusion-proof and substantially corrosion-resistant material, said first layer and said second layer being joined together with said layer of biocompatible material comprising an exterior wall of said first part;
  a second part, closing an upper opening in said first part, and comprised of at least said biocompatible material;
  a partition wall disposed in said receptacle in said first part, said partition wall comprising a substantially diffusion-proof, corrosion-resistant material and forming a first closed space in said first part in which said battery is disposed with said partition wall and a portion of said first part constituting a casing for said battery, said casing being an integral part of said first part;
  said partition wall and said second part forming a second closed space in said first part in which said electronics unit is disposed;
  said battery having first and second poles and said battery being in direct contact with said second layer of said first part, with said second layer comprising a first of the poles of said battery and being connected to said electronics unit; and
  a feed-through extending through said partition wall for connecting a second of the poles of the battery to said electronics unit.

19. A battery unit for a medical implant comprising:
  a first part comprising at least in part a multi-layer material having a first layer consisting of a biocompatible material and a second layer consisting of a substantially diffusion-proof and corrosion-resistant material, said first and second layers being joined together with said first layer forming an exterior wall of said first part, said first part forming a receptacle;
  a battery disposed in said receptacle;
  a cover hermetically closing said receptacle and comprising at least one layer of a substantially diffusion-proof and corrosion-resistant material and forming a closed space, with said first part, in which said battery unit is disposed and constituting a battery casing;

said battery having first and second poles and said second layer comprising one of said poles of said battery; and an insulated feed-through disposed in said cover connected to a second of said poles of said battery.

20. A method for manufacturing a casing for an active medical implant comprising:

selecting a first sheet layer of a biocompatible material;

selecting a second sheet layer of a substantially diffusion-proof, corrosion-resistant metal;

rolling said first and second sheet layers together to form a composite, multi-layer sheet;

forming said composite, multi-layer sheet in a bowl-shaped receptacle having an interior with said second sheet layer facing said interior;

placing a battery in said receptacle;

providing a second part having at least a surface comprised of a substantially diffusion-proof, corrosion-resistant metal; and hermetically sealing said receptacle with said battery therein with said cover with said surface of said cover facing said interior of said receptacle and thereby completely surrounding said battery in said receptacle with substantially diffusion-proof, corrosion-resistant metal.

21. A method as claimed in claim 20 wherein the step of selecting a second sheet layer comprises selecting a second sheet layer of a substantially diffusion-proof corrosion-resistant metal selected from the group consisting of stainless steel, nickel and Cr-Ni steel.

22. A method as claimed in claim 20 wherein the step of selecting a second sheet layer comprises selecting a second sheet layer comprised of 304L stainless steel.

23. A method as claimed in claim 20 wherein the step of providing a cover comprises providing a cover having at least a surface comprised of a substantially diffusion-proof, corrosion-resistant metal selected from the group consisting of stainless steel, nickel and Cr-Ni steel.

24. A method as claimed in claim 20 wherein the step of providing a cover comprises providing a cover having at least a surface comprised of 304L stainless steel.

* * * * *